United States Patent [19]

Laus

[11] Patent Number: 4,798,602
[45] Date of Patent: Jan. 17, 1989

[54] DISPOSABLE LIQUID-ABSORBENT PRODUCTS

[75] Inventor: Guy G. Laus, Rixensart, Belgium

[73] Assignee: Exxon Chemical Patents Inc., Linden, N.J.

[21] Appl. No.: 836,261

[22] Filed: Mar. 4, 1986

[51] Int. Cl.$^4$ .................. A61F 13/16; A61F 13/18; A61F 13/20

[52] U.S. Cl. .................. 604/372; 428/500; 428/507

[58] Field of Search ............... 428/500, 507; 604/359, 604/360, 365, 379, 372, 373

[56] References Cited

U.S. PATENT DOCUMENTS

| | | | |
|---|---|---|---|
| 1,953,526 | 12/1928 | Ainslie | 604/359 |
| 3,340,875 | 9/1967 | Dudley et al. | 604/359 |
| 3,665,920 | 5/1972 | Davis | 604/370 |
| 3,783,871 | 1/1974 | Sabee | 604/372 |
| 3,814,101 | 6/1974 | Kozak | 604/370 |
| 3,886,941 | 6/1975 | Duane et al. | 604/370 |
| 3,901,240 | 8/1975 | Hoey | 604/359 |
| 3,987,792 | 10/1976 | Henandez et al. | 604/372 |
| 4,009,313 | 2/1977 | Crawford et al. | 604/375 |
| 4,041,949 | 8/1977 | Kozak | 604/370 |
| 4,045,833 | 9/1977 | Mesek et al. | 604/370 |
| 4,097,943 | 7/1978 | O'Connell | 604/372 |
| 4,296,750 | 10/1981 | Woon et al. | 604/370 |
| 4,376,799 | 3/1983 | Tusim | 428/213 |
| 4,476,180 | 10/1984 | Wnuk | 428/220 |
| 4,522,203 | 6/1985 | Mays | 428/212 |
| 4,595,629 | 6/1986 | Mays | 728/286 |

Primary Examiner—C. Fred Rosenbaum
Assistant Examiner—Jerome R. Smith, Jr.
Attorney, Agent, or Firm—R. L. Graham

[57] ABSTRACT

The use in an absorbent product of a liquid impervious layer comprising an elastomeric film comprising an ethylene homopolymer and/or copolymer and an olefinic elastomer.

3 Claims, 1 Drawing Sheet

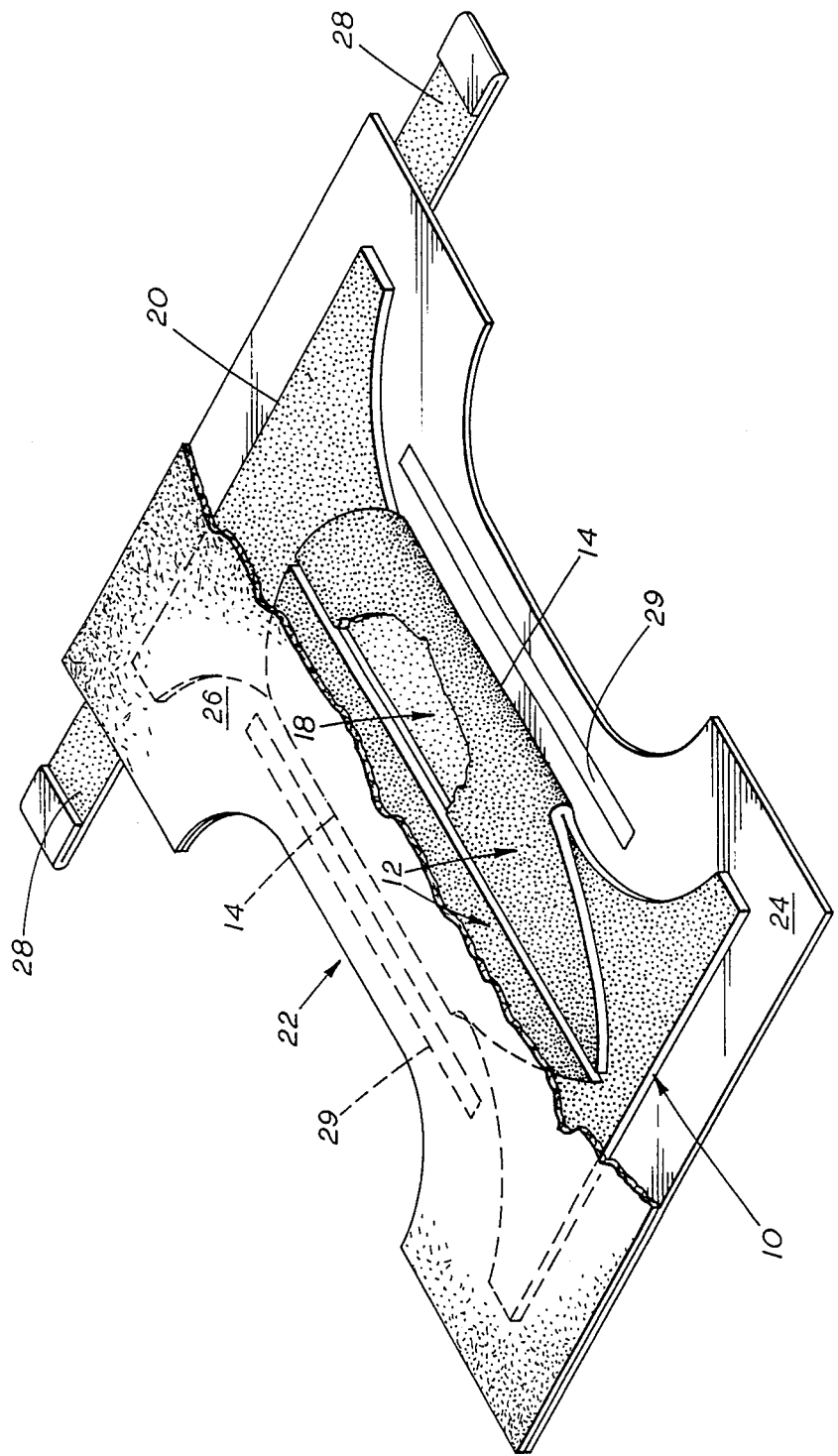

DISPOSABLE LIQUID-ABSORBENT PRODUCTS

This invention relates to disposable absorbent products, in particular for use in the field of hygiene.

Various constructions of liquid-absorbent products such as disposable diapers for babies and adults ("nappies"), bed pads, hospital medical and surgical pads and sanitary napkins are known in the art which include a body contacting layer of liquid-pervious materials, an outer liquid-impervious layer and an intermediate liquid-absorbent component which preferably when wetted absorbs many times its own weight of liquid. This absorbent material may be a gel-forming material or a fluffed fibrous pulp or creped, laminated or single ply wadding.

The outer layer has traditionally been formed of a polyolefinic type film and particularly of a polyethylene film (e.g. EP No. 0 063 331 or EP No. 0 082 727), or of a tissue paper impregnated with a water-proofing agent (e.g. U.S. Pat. No. 3 903 889). GB No. 2 115 702 uses a vapour-permeable, liquid impermeable film comprising of polyolefin, filler and liquid or wax-like hydrocarbon polymer or liquid rubber, which film is then stretched. The principal functions of the outer layer is to retain moisture (e.g. urine) or faecal matter in the absorbent component. In order to prevent leakages the outer layers have also been designed with inserts such as waist and leg elastomeric strips and bands. The outer layer also dictates how the absorbent product feels when it is in use. Traditional products have not been entirely satisfactory in that they make the wearer uncomfortable. They also have the additional drawback of being noisy when worn.

It has been discovered that an elastomeric film may be used as the outer layer in absorbent products. The elastomeric film may replace polyolefinic film or tissues as the outer layer of such products and this invention relates to such replacement. The elastomeric film avoids the need for stretching or orienting processes and thus simplifies product preparation.

The present invention is concerned with improvements in the construction of liquid-absorbent products of the type which are disposable as, for example, by flushing in a toilet system. As used herein "absorbent products" includes diapers for babies and adults, bed pads, hospital medical and surgical pads and sheets, catamenial devices such as sanitary napkins, continuous filament material such as sutures and products of similar description which are used for absorbing body liquids. While various embodiments of the invention are described herein in terms of disposable diaper construction, it will be understood that the invention is applicable in its broadest aspects to other types of liquid-absorbent products.

Thus, in one aspect this invention provides the use in an absorbent product of a liquid impervious layer comprising an elastomeric film comprising an ethylene homopolymer and/or copolymer and an olefinic elastomer.

The ethylene homopolymer and/or copolymer is preferably a polyethylene or an ethylene copolymer formed with an unsaturated comonomer such as an alpha-olefin, a vinyl ester or an olefinically unsaturated acid or ester. The polyethylene may be a low, medium or high density polymer and may be formed by a high pressure, radical process or by a Ziegler catalysed process. Thus, for example, suitable polyethylene include conventional low density polyethylene formed by a high pressure process (LDPE) or the more linear, low density polyethylene prepared by Ziegler catalysed polymerization (LLDPE). More preferably an ethylene copolymer such as ethylene/vinyl acetate, ethylene/acrylic acid, ethylene/methacrylic acid ethylene/methyl acrylate or ethylene/butyl acrylate copolymers may be used. Particularly preferred copolymers are ethylene/vinyl acetate copolymers (EVAs) containing from 9 to 40% by weight of vinyl acetate. Preferably such EVAs have a melt index (ASTM D 1238E) of from 0.1 to 10 g/10 mins, most preferably from 1.to 5 g/0 mins.

The olefinic elastomer component is elastomeric and therefore non-liquid and it may be an ethylenepropylene elastomer (EPM) or an ethylene-propylene-diene elastomer (EPDM). The non-conjugated diene in the EPDM may be, for example, 1,4-hexadiene, dicyclopentadiene or ethylidene norbornene. The elastomers used in the invention preferably have an ethylene content of from 45 to 80 wt % and a Mooney viscosity [ML 1+8 at 127° C.] of from 15 to 80. The invention can employ as the elastomer component various alternative elastomers such as polyisobutylene (PIB), isobuylene-isoprene rubbers (IIR) and halogenated derivatives thereof, thermoplastic rubbers such as styrene-butadiene-styrene block copolymer rubbers (SBS), and these may be employed alone or in combination with EPM or EPDM.

In a preferred aspect the outer layer comprises a film formd from an elastomeric polymer blend composition comprising:

(a) 25 to 55 parts by weight of an EPM or EPDM elastomer;
(b) 35 to 55 parts by weight of ethylene-vinyl acetate copolymer resin containing 9 to 40% by weight vinyl acetate; and
(c) 5 to 25 parts by weight of a normally liquid hydrocarbon process oil, the oil preferably being an aromatic, highly aromatic, naphthenic or paraffinic process extender oil, the blend composition preferably containing at least 4.5% by weight of vinyl acetate based upon the weight of the total composition and the blend composition preferably having a melt index at 190° C. of 0.5 to 15.0 g/10 min.

A further embodiment of the present invention comprises the aforesaid (a), (b) and (c) ingredients, together with (d) 0 to 30 parts by weight of calcium carbonate as a filler and opacifying agent and (e) 0 to 2% by weight of a film processing slip agent or abherent based upon the weight of the total blend composition.

Hydrocarbon oils useful in the present invention function as process aids whose activity is uniquely enhanced in the presence of vinyl acetate copolymers, as plasticizers producing low modulus and enhanced elasticity in the solid state and those useful are the normally liquid hydrocarbon processing and extender oils (ASTM D 2226) categorized as aromatic, naphthenic and paraffinic process oils of a medium viscosity range. Oils sold under the trademarks "Flexon", "Sunpar", "Marcol" and "Primol" have been found especially useful.

Preferred films are those containing EPM or EPDM elastomers having at least 60 weight percent ethylene and a molecular weight sufficient to provide a Mooney viscosity of from 20 to 60 ASTM D 1646 (ML 1+8 at 127° C). Preferred ethylene-vinyl acetate copolymers are those containing 14% to 28% by weight vinyl acetate. Aromatic, naphthenic or paraffinic hydrocarbon plasticizer oils may be used. Paraffinic and naphthenic grades are commonly lighter in colour and lower in odour and therefore preferable. Aromatic oils are generally more compatible with other components and exhibit less surface migration when used at high percentages.

Calcium carbonate is an optional material for use in the compositions of the present invention and functions chiefly as a filler to reduce component cost. It may be used in fairly substantial amounts, up to 30 parts by weight. It has been found useful in reducing film blocking, and it will impart an off-white cloudy appearance to the film. Calcium carbonate will also reduce tackiness in the finished film product.

Film processing slip agents or abherents are optional but preferable components of the compositions of the present invention. These materials are well known in the art and are commonly employed in film manufacture as processing aids. Numerous materials are suitable but stearic acid and stearic acid derivatives such as calcium or zinc stearate or stearamide are particularly preferred. Other suitable abherents include the $C_{12}$–$C_{22}$ fatty acids and fatty acid amides and metal soaps, such as erucamide, silicones and natural and manufactured waxes such as glyceryl and glycol stearates, as well as inorganic abherent materials.

Most preferred proportions for preparing the blends of the present invention are (a) 25–50 parts by weight of EPM or EPDM; (b) 40–55 parts by weight of ethylenevinyl acetate copolymer; (c) 5–25 parts by weight of hydrocarbon oil and 0.1 to 1.0% by weight of abherent, such as stearic acid or a fatty acid amide. A preferred film composition containing calcium carbonate filler comprises:

(a) 35 to 45 parts by weight of an EPM or EPDM elastomer having an ethylene content of from 45 to 80 weight percent;
(b) 35 to 50 parts by weight of a thermoplastic ethylene-vinyl acetate copolymer having a vinyl acetate content of 9 to 40% by weight;
(c) 5 to 20 parts by weight of a normally liquid hydrocarbon process oil, the oil being an aromatic, naphthenic or paraffinic or extender oil;
(d) 2 to 15 parts by weight of filler such as calcium carbonate; and
(e) 0 to 1% by weight, based on the total composition, of a film processing abherent, the blend composition containing at least 4.5% by weight vinyl acetate based upon the total weight of the blend composition and the blend composition having a melt index at 190° C. (2.16 kg load) of 0.5 to 15 g/10 min.

The invention may have the following advantages versus conventional films or tissues used as outer layers
 Substantial elimination of noise (high degree of silence)
 Reduction of the cold plastic-like feeling
 Reduction in leakage problems currently requiring elastomeric strips and bands
 Higher degree of comfort resulting from the elastic nature of the outer layer
 Less movement of the product as a result of controlled surface friction of the outer layer In another aspect this invention provides a disposable liquid absorbent garment comprising, in combination:
(a) a liquid impermeable outer layer comprising an elastomeric film as defined herein;
(b) a liquid permeable liner; and
(c) between the outer layer and the liner an absorbent layer.

In one embodiment of the invention there is provided a disposable diaper having a body contacting layer of any suitable material having liquid-pervious character and which is preferably of fine and soft texture to provide a reasonable measure of comfort to the wearer. Such layer could be a woven or a non-woven fabric and it could be of cotton, rayon, paper, synthetic materials, etc and could be of plural ply structure. The diaper also includes an outer layer as defined herein. Intermediate the body contacting and outer layer there is provided an absorbent layer, preferably of fluffed pulp material such as a core of fibrous cellulosic or other material.

The invention will now be described in more detail though only by way of illustration, with reference to the accompanying drawing which shows a preferred disposable diaper incorporating the outer layer of the present invention. An absorbent layer 10 is folded along lines 14 to provide a double thickness of absorbent in area 12. Prior to folding, a gel-forming material may be incorporated by placement at 18 near the front edge 20 of layer 10. The layer 10 is incorporated into the diaper 22 between liquid impermeable outer layer 24 and liquid permeable liner 26. Outer layer 24 is provided with fastening means 28 which may be, for example, self-adhesive tape or ties. Elastic means 29 may be provided to aid in fluid retention within the diaper structure, but it is an advantage of the invention that such additional aids are not generally necessary. The liner 26 may be a nonwovern material such as spunbonded polypropylene, a carded web, or a split or fibrillated film.

The following Examples are now given, again only by way of illustration, to show certain aspects of the invention in more detail.

EXAMPLE 1

An outer layer for use in a disposable diaper was prepared by blowing a tubular film from the following composition:

|  | wt % |
|---|---|
| EPDM elastomer (Vistalon 3708) | 38 |
| EVA 26% VA; melt index = 2) | 40 |
| Filler (calcium cabonate) | 5 |
| White oil | 16 |
| Processing additive | 1 |
| 500–1000 ppm of antioxidant were also added | |

The tubular film may be cut to form an outer layer for a diaper in the manner shown in the accompanying drawing.

EXAMPLE 2

The procedure of Example 1 was repeated but using a film prepared from:

|  | wt % |
|---|---|
| EPDM elastomer (Vistalon 3708) | 41 |
| EVA (26% VA; melt index = 2) | 45 |
| Filler (calcium carbonate) | 5 |
| White oil | 8 |
| Processing additive | 1 |
| 500–1000 ppm antioxidant were also added | |

Diapers made using the films of Examples 1 and 2 as outer layers were judged to be more comfortable and less noisy than those using conventional outer layers.

I claim:

1. A disposable liquid absorbent garment comprising in combination
   (a) a liquid impervious outer layer comprising a blend of
      (i) 25 to 55 parts by weight of Ethylene Propylene (EPM) or Ethylene Propylene Diene (EPDM) elastomer having an ethylene content of 45 to 80 weight percent;
      (ii) 35 to 55 parts by weight of a thermoplastic ethylene-vinyl acetate copolymer having a vinyl acetate content of 9 to 40% by weight;
      (iii) 5 to 25 parts by weight of a normally liquid hydrogen process oil, the oil being an aromatic, highly aromatic napthenic or paraffinic or extender oil;
      (iv) 0 to 30 parts by weight of calcium carbonate filler, and
      (v) 0 to 2% by weight, based on the total composition, of a film processing adherent;
      the blend composition containing at least 4.5% by weight vinyl acetate blend upon the total weight of the blend composition and the blend composition having a melt index at 190° C. (2.16 kg load) of 0.5 to 15 g/10 min.;
   (b) a liquid permeable liner; and
   (c) an intermediate absorbent layer having one side in contact with the liquid impervious outer layer and its opposite side in contact with the liquid permeable liquid liner.

2. A garment as claimed in claim 1, in which said ethylene/vinyl acetate copolymer has a melt index of from about 0.1 to about 10 g/10 mins (ASTM D1238E).

3. The product garment as claimed in claim 1, in which said elastomer has a Mooney viscosity [ML 1+8 at 127° C.] of from about 15 to about 80.

* * * * *